United States Patent
Perry

Patent Number: 6,043,388
Date of Patent: Mar. 28, 2000

[54] METHOD FOR PREPARATION OF ORGANOHYDROGEN POLYSILOXANES

[75] Inventor: Robert J. Perry, Niskayuna, N.Y.

[73] Assignee: General Electric Company, Pittsfield, Mass.

[21] Appl. No.: 09/217,650

[22] Filed: Dec. 21, 1998

[51] Int. Cl.$^7$ ....................................................... C07F 7/08
[52] U.S. Cl. ................................................................ 556/451
[58] Field of Search ............................................. 556/451

[56] References Cited

U.S. PATENT DOCUMENTS

| | | | |
|---|---|---|---|
| 5,011,962 | 4/1991 | Staiger et al. | 556/453 |
| 5,446,185 | 8/1995 | Cobb et al. | 556/451 |
| 5,493,040 | 2/1996 | Cobb et al. | 556/451 |
| 5,866,707 | 2/1999 | Herzig | 556/451 |

OTHER PUBLICATIONS

Yoshino, K. Kawamata, A., JP 02306980A2 to Kao Corp, Dec. 20, 1990—reaction of cyclic trimer with water chlorodimethylsilane, $SliO_2$ and hexane.

Andrianov, K.A., et al. *J. Gen. Chem. USSR (Engl. Transl.)*, 1971, 41;603–605, reaction of the dipotassium salt of hexamethyltrisiloxane diol and chlorodimethylsilane.

Zhandov, A.A., et al. *J. Gen. Chem. USSR (Engl. Transl.)* 1973, 43, 1265–1269, the ring opening reaction of octamethylcyclotetrasiloxane and tetramethyldisiloxane with sulfuric acid with an ion exchange resin (Schindler, S.; Ruehlmann, K., *Plaste Kautsch.*) 1978,25,384–3850).

Gustavson, W.A.; Epstein; P.S.; Curtis, M.D., *J.Organometal. Chem.*, 1982, 238,87–97, the redistribution reaction of tetramethyldisiloxane with cyclometallodisiloxane complexes.

Sakiyama, M.; Okawara, R., *J. Organometal, Chem.*, 1964, 2, 473–477.

*Primary Examiner*—Paul F. Shaver

[57] ABSTRACT

A method comprising the solventless reaction of a 1,1,3,3-tetraalkyldisiloxane ($HR_2Si$—O—$Si\ R_2H$) with a hexaalkycyclotrisiloxane ($R'_2SiO)_3$ in the presence of linear phosphonitrilic chloride to produce $$(HR_2SiO)(SiR'_2O)_3(SiR_2H)$$

wherein R and R' are independently monovalent alkyl or haloalkyl groups, preferably wherein R and R' are monovalent hydrocarbons having from one to three carbons. Appropriate selection of reaction conditions results in no or minimal equilibration of the desired product to the homologous materials.

14 Claims, No Drawings

METHOD FOR PREPARATION OF ORGANOHYDROGEN POLYSILOXANES

BACKGROUND OF THE INVENTION

This invention relates to methods for the manufacture of polysiloxanes. In particular, this invention relates to a method for the manufacture of low molecular weight organohydrogen polysiloxanes by ring opening.

Silicones and cured silicone elastomers have a wide variety of commercially important applications, including as greases, adhesives, sealants, coatings, gaskets, encapsulants, potting compounds, and molding materials. Most of these polymers are manufactured from low molecular weight silicone oligomers. Organohydrogen polysiloxanes in particular are used in the synthesis of silicone polymers, and to cross-link a wide variety of resins to form silicone elastomers. Of these, hydride stopped dimethyl siloxanes having the formula $(HMe_2SiO)(SiMe_2O)_x(SiHMe_2)$ $(M^HD_xM^H)$, and in particular these hydride stopped dimethyl siloxanes wherein x is 3 form the backbone for durable, hydrophilic silicone elastomers.

A number of methods for the manufacture of $M^HD_xM^H$ have been reported. For example, K. Yoshino and A. Kawamata have reported synthesis by reaction of a cyclic trimer with water, chlorodimethylsilane, $SiO_2$, and hexane, in JP 02306980 A2 (Dec. 20, 1990). Reaction of the dipotassium salt of hexamethyltrisiloxane diol and chlorodimethylsilane has been reported by K. A. Andrianov et al., in J. Gen. Chem. USSR (Engl. Transl.), Vol. 41, pp. 603–605 (1971).

Ring opening of octamethylcyclotetrasiloxane in the presence of 1,1,3,3-tetramethyldisiloxane with sulfuric acid has been reported by A. A. Zhandov et al. in J. Gen. Chem. USSR (Engl. Transl.), Vol. 43, pp. 1265–1269 (1973); and with an ion exchange resin by S. Schindler, and K. Ruehlmann in Plaste Kautsch., Vol. 25, pp. 384–385 (1978); and with active clays by M. Sakiyaja and R. J. Okawara in Organometal. Chem., Vol. 2, pp. 473–477 (1964).

The redistribution reaction of tetramethyldisiloxane with cyclometallodisiloxane complexes has been reported by W. A. Gustavson, P. S. Epstein, and M. D. Curtis in J. Organometal. Chem., Vol. 238, pp. 87–97 (1982). Ring opening and equilibration of 1,1,2,2-tetramethyldisiloxane $(M^HM^H)$ and octamethylcyclotetrasiloxane $(D_4)$ with an acidic clay such as FILTROL™ results in a statistical mixture of products.

Despite the number of routes attempted or known to produce $M^HD_xM^H$, all have various drawbacks and disadvantages, in that they are either complex, expensive, or difficult to run. Most require a solvent, which increases the cost of the reaction, as well as creates disposal issues. Accordingly, there remains a need in the art for simple, preferably solventless methods for the manufacture of $M^HD_xM^H$, especially wherein x is three.

SUMMARY OF THE INVENTION

The above-described and other disadvantages of the prior art are alleviated by the present method, comprising reaction of a 1,1,3,3-tetraalkyldisiloxane ($HR_2Si$—O—$SiR_2$) with a hexaalkylcyclotrisiloxane $(R'_2SiO)_3$ in the presence of an acid source to produce $(HR_2SiO)(SiR'_2O)_3(SiR_2H)$ wherein R and R' are independently monovalent alkyl or halogen-substituted alkyl groups.

DETAILED DESCRIPTION OF THE INVENTION

The present method comprises the solventless reaction of a 1,1,3,3-tetraalkyldisiloxane ($HR_2Si$—O—$SiR_2H$) with a hexaalkycyclotrisiloxane $(R'_2SiO)_3$ in the presence of an acid source to produce $(HR_2SiO)(SiR'_2O)_3(SiR_2H)$ wherein R and R' are independently monovalent alkyl groups having from 1 to 12 carbons, such as methyl, ethyl, propyl, isopropyl, n-butyl, and the like, or halogen-substituted alkyl groups having from 1 to 12 carbons, for example trifluoromethyl, pentafluoroethyl, 3,3,3-trifluoropropyl, and the like. Preferably, R and R' are independently monovalent alkyl groups having from one to three carbons, and most preferably, R and R' are each methyl groups.

As used herein,

M is $R^1_3SiO_{1/2}$, wherein $R^1$ is a methyl group;

$M^H$ is $HR^1_2SiO_{1/2}$, wherein H is hydrogen $R^1$ is a methyl group;

D is $R^2_2SiO_{2/2}$, wherein $R^2$ is a methyl group;

$D_3$ is $(R^2_2SiO_{2/2})_3$, wherein $R^2$ a methyl group; and $D^H$ is $R^2HSiO_{2/2}$, wherein H is hydrogen and $R^2$ is a methyl group.

It is to be understood that while the following discussion is directed to species wherein $R^1$ and $R^2$ are each methyl groups, those species wherein $R^1$ and $R^2$ are each independently monovalent hydrocarbons having from 1 to 12 carbons, for example methyl, ethyl, propyl, isopropyl, n-butyl, and the like, or monovalent halogenated hydrocarbons having from 1 to 12 carbons, for example trifluoromethyl, pentafluoroethyl, 3,3,3-tripfluoropropyl, and the like, are also within the scope of the present invention.

In a preferred embodiment, 1,1,2,2-tetramethyldisiloxane $M^HM^H$) is reacted with hexamethylcyclotrisiloxane $(D_3)$ in the presence of an acid source to produce $(HMe_2SiO)(SiMe_2O)_{3x}(SiMe_2H)$ $(M^HD_{3x}M^H)$ wherein Me is a methyl group and x is an integer of at least one. In an important feature of this method, the inventors hereof have surprisingly found that appropriate selection of an acid source for the ring-opening results in no or minimal equilibration of the product $M^HD_3M^H$ to the homologous $M^HD_{3x}M^H$ materials.

Appropriate acid sources will generally have $pK_a$'s in the range from about 0 to about –10. Such acids include, but are not limited to, sulfonic acids such as methanesulfonic acid ($CH_3SO_3H$) and toluene sulfonic acid ($H_3CC_6H_4SO_3H$), and linear phosphonitrilic chloride (hereinafter "LPNC"), available from Wright Corporation, Willington, N.C. LPNC is an acidic catalyst which has been used in condensation and disproportionation reactions. For example, LPNC has been used in the ring opening of cyclic methylhydrogen siloxanes in the presence of hexamethyldisiloxane (MM) to generate a homologous series of $MD^H_xM$ oligomers. Since no statistical preference for the desired $MD^H_{4x}M$ was observed in this reaction, it is a surprising and unexpected result that use of LPNC (or other acids) under the appropriate conditions yields ring opened, hydride stopped products without significant equilibration to $M^HD_xM^H$ homologs.

In order to determine the reaction scope and preferred parameters, a series of experiments were performed with varying $M^H$:D ratios, reaction temperatures, acid sources, and alkylcyclosiloxane (D) sources.

As is described in Example 1, equimolar mixtures of cyclic trimer ($D_3$), 1,1,2,2-tetramethyldisiloxane ($M^H M^H$) and a catalytic amount of LPNC are mixed and stirred at 50° C. Samples are removed from the mixture at timed intervals for gas chromatography (GC) analysis. After 15 minutes, the reaction comprised 8% $M^H M^H$, 58% of the desired $M^H D_3 M^H$, 22% $M^H D_6 M^H$ and 6% $M^H D_9 M^H$. Less than 1% $D_3$ was observed to be present, as well as very little $M^H DM^H$, $M^H D_2 M^H$, $M^H D_4 M^H$ or other chain scission products. After one hour, less $M^H D_3 M^H$ but more chain extended products were observed, and after 17 hours, an entire series of $M^H D_x M^H$ materials had formed.

Using a 1:2 ratio of $D_3$ to $M^H M^H$ (Example 2), after 40 hours at ambient temperature, the reaction comprised 32% $M^H M^H$, 55% $M^H D_3 M^H$, and 5% $M^H D_6 M^H$. Less than 1% $M^H D_9 M^H$ was seen in the reaction mixture. At the same 1:2 ratio of $D_3$ to $M^H M^H$ (Example 3), after twenty-four hours at 50° C. 24% $M^H M^H$, 59% $M^H D_3 M^H$, 8% $M^H D_6 M^H$ and less than 1% $M^H D_9 M^H$ were observed by GC.

Example 4 illustrates the effect of a one hundred-fold scale-up using the reaction conditions of Example 3 (50° C., 1:2 ratio of $D_3$ to $M^H M^H$). The distribution of products was observed to be 33% $M^H M^H$, 52% $M^H D_3 M^H$, and 5% $M^H D_6 M^H$. Neutralization with MgO, followed by stripping yielded $M^H D_3 M^H$ of 78% purity.

These results are superior to preparation of $M^H D_3 M^H$ by hydrolysis of 2 moles of chlorodimethylsilane with 3 moles of dichlorodimethylsilane in the presence of water (Comparative Example 7). The products obtained thereby comprises 2% $M^H M^H$, 5% $M^H DM^H$, 19% $M^H D_2 M^H$, 35% $M^H D_3 M^H$, 13% $M^H D_4 M^H$, 9% $M^H D_5 M_H$ and 4% $M^H D_6 M^H$.

Comparable product ratios were obtained when acid washed clay was used as a catalyst (Comparative Example 8). However, the rate of equilibration and redistribution was much faster than that for LPNC, and resulted in poorer yields of the desired $M^H D_3 M^H$ product.

As shown in Example 5, a cyclic trimer is selectively opened in the presence of a cyclic tetramer. Thus, when an equimolar mixture of $D_3$, octamethylcylcotetrasiloxne ($D_4$) and $M^H M^H$ is reacted in the presence of LPNC, the reaction mixture consists of 43% unreacted tetramer, 34% $M^H D_3 M^H$, 12% $M^H D_6 M^H$ and less than 3% $M^H D_9 M^H$, along with small amounts of $M^H D_x M^H$ products. The starting GC ratio of material was 43% $D_4$, 35% $D_3$ and 21% $M^H M^H$.

In comparison of the ring opening of $D_3$, reaction of $D_4$ with $M^H M^H$ results in very slow opening of the cyclic tetramer, and produces the homologous series of $M^H D_x M^H$ materials (Example 6). After 65 hours at 50° C., the ratio of products was found to be 13% $M^H M^H$, 13% $M^H DM^H$, 33% $D_4 + M^H D_2 M^H$, 11% $M^H D_3 M^H$, 17% $M^H D_4 M^H$, 5% $M^H D_5 M^H$, 3% $M^H D_6 M^H$ and 2% $M^H D_7 M^H$.

Examples 10 and 13 illustrate that sulfonic acids are also appropriate acids for the ring-opening reaction described herein. Under the present reaction conditions, trifluoroacetic acid leads to rapid equilibration While it is preferred to perform the reaction in a solventless environment, the ring opening will also proceed without rapid equilibration in the presence of a solvent (tetrahydrofuran), as shown in Example 12. Inert solvents such as hexane, heptane, cylcohexane, benzene, toluene, xylene, methylene chloride, chloroform, chlorobenzene, diethyl ether, diphenyl ether, tetrahydrofuran, dioxane or acetonitrile are suitable.

The following Examples are provided by way of illustration only, and should not be read to limit the scope of the invention.

EXAMPLE 1

Cyclic trimer ($D_3$, 2.5 g, 11.2 mmol), 1,1,3,3-tetramethyldisiloxane ($M^H M^H$, 1.4 g, 11.2 mmol) and LPNC (linear phosphonitrilic chloride, 50 µl as a 2% solution in 50 cstk dimethylsilicone oil, 250 ppm catalyst) were mixed together and stirred at 50° C. Samples were removed at timed intervals for GC analysis. After 15 minutes, 8% $M^H M^H$, 58% $M^H D_3 M^H$, 22% $M^H D_6 M^H$ and 6% $M^H D_9 M^H$ were seen in the reaction mixture. Less than 1% $D_3$ and very little $M^H DM^H$, $M^H D_2 M^H$, $M^H D_4 M^H$ or other chain scission products were present.

EXAMPLE 2

Cyclic trimer ($D_3$, 2.5 g, 11.2 mmol), 1,1,3,3-tetramethyldisiloxane ($M^H M^H$, 2.8 g, 22.4 mmol) and LPNC (linear phosphonitrilic chloride, 20 µl as a 2% solution in 50 cstk dimethylsilicone oil, 75 ppm catalyst) were mixed and stirred at ambient temperature. Samples were removed at timed intervals for GC analysis. After 2 days, 32% $M^H M^H$, 55% $M^H D_3 M^H$, and 5% $M^H D_6 M^H$ were seen in the reaction mixture with less than 6% $D_3$ present and very little $M^H DM^H$, $M^H D_2 M^H$, $M^H D_4 M^H$ and other chain scission products present.

EXAMPLE 3

Cyclic trimer ($D_3$, 2.5 g, 11.2 mmol), 1,1,3,3-tetramethyldisiloxane ($M^H M^H$, 2.8 g, 22.4 mmol) and LPNC (linear phosphonitrilic chloride, 20 µl as a 2% solution in 50 cstk dimethylsilicone oil, 75 ppm catalyst) were mixed and stirred at 50° C. Samples were removed at timed intervals for GC analysis. After 24 hours, 24% $M^H M^H$, 59%, $M^H D_3 M^H$, and 8% $M^H D_6 M^H$ were seen in the reaction mixture with less than 6% $D_3$ present and very little $M^H DM^H$, $M^H D_2 M^H$, $M^H D_4 M^H$ and other chain scission products.

EXAMPLE 4

Cyclic trimer ($D_3$, 250 g, 1.12 mol), 1,1,3,3-tetramethyldisiloxane ($M^H M^H$, 280 g, 2.25 mole) and LPNC (linear phosphonitrilic chloride, 2.6 g as a 2% solution in 50 cstk dimethylsilicone oil, 100 ppm catalyst) were mixed together and stirred at 50° C. Samples were removed at timed intervals for GC analysis. After 48 hours, 33% $M^H M^H$, 52% $M^H D_3 M^H$, and 5% $M^H D_6 M^H$ and <1% $M^H D_9 M^H$ were present. Neutralization of the mixture with MgO, followed by removal of the solvent yielded $M^H D_3 M^H$ of 78% purity.

EXAMPLE 5

Cyclic trimer ($D_3$, 2.5 g, 11.2 mmol), cyclic tetramer (3.3 g, 11.2 mmol), 1,1,3,3-tetramethyldisiloxane ($M^H M^H$, 1.7 g, 11.2 mmol) and LPNC (linear phosphonitrilic chloride, 30 µl as a 2% solution in 50 cstk dimethylsilicone oil, 42 ppm catalyst) were added together and stirred at 50° C. Samples were removed at timed intervals for GC analysis. After 4 hours, the reaction mixture consisted of 43% unreacted tetramer, 34% $M^H D_3 M^H$, 12% $M^H D_6 M^H$ and less than 3% $M^H D_9 M^H$, along with small amounts of $M^H D_x M^H$ products.

EXAMPLE 6 (COMPARATIVE)

Cyclic tetramer ($D_4$, 3.3 g, 11.2 mmol), 1,1,3,3-tetramethyldisiloxane ($M^H M^H$, 2.5 g, 20.1 mmol) and LPNC (linear phosphonitrilic chloride, 40 µl as a 2% solution in 50 cstk dimethylsilicone oil, 140 ppm catalyst) were mixed together and stirred at 50° C. Samples were removed at timed intervals for GC analysis. After 65 hours at 50° C., the ratio of products was 13% $M^H M^H$, 13% $M^H DM^H$, 33% $D_4 + M^H D_2 M^H$, 11% $M^H D_3 M^H$, 17% $M^H D_4 M^H$, 5% $M^H D_5 M^H$, 3% $M^H D_6 M^H$ and 2% $M^H D_7 M^H$.

EXAMPLE 7 (COMPARATIVE)

Cyclic trimer ($D_3$, 2.5 g, 11.2 mmol), 1,1,3,3-tetramethyldisiloxane ($M^HM^H$, 2.8 g, 22.4 mmol) and acid treated clay (FILTROL™ F-20 from Englehardt, 50 mg, 1 wt %) were mixed together and stirred at 50° C. Samples were removed at timed intervals for GC analysis. After 18 hours, 19% $M^HM^H$, 20% $M^HDM^H$, 19% $M^HD_2M^H$, 14% $M^HD_3M^H$, 10% $M^HD_4M^H$, 7% $M^HD_5M^H$ and 3% $M^HD_7M^H$ were present.

EXAMPLE 8 (COMPARATIVE)

A blend of dichlorodimethylsilane (20.4 g, 0.16 mole) and chlorodimethylsilane (9.8 g, 0.10 mole) was added to cooled water (45.2 g) and stirred. When hydrolysis was complete, the mixture was washed with brine and the silicone layer separated and analyzed by GC. The silicone layer comprised 2% $M^HM^H$, 5% $M^HDM^H$, and 19% $M^HD_2M^H$, 35% $M^HD_3M^H$, 13% $M^HD_4M^H$, 9% $M^HD_5M^H$, and 4% $M^HD_6M^H$.

EXAMPLE 9 (COMPARATIVE)

A mixture of $M^HM^H$ (95.13 g), a silanol fluid with ~3000 cstk viscosity (CRTV942 from GE Silicones, 161.96 g) and LPNC (1.29 g of 2 wt % solution in 50 cstk dimethylsilicone oil) was heated to 80–90° C. for 2.5 h to yield an equilibrium mixture having the composition 15%, $M^HM^H$, 11% $M^HDM^H$, 9% $M^HD_2M^H$, 8% $M^HD_3M^H$, 7% $M^HD_4M^H$, 7% $M^HD_5M^H$, and others.

EXAMPLE 10

Cyclic trimer ($D_3$, 2.5 g 11.2 mmol), 1,1,3,3-tetramethyldisiloxane ($M^HM^H$, 2.8 g, 22.4 mmol) and p-toluenesulfonic acid (3 mg) were mixed together and stirred at 50° C. Samples were removed at timed intervals for GC analysis. After 24 hours, the reaction mixture comprised 21.7% $M^HM^H$, 1.8% $D_3$, 70.0% $M^HD_3M^H$ and 3.2% $M^HD_6M^H$.

EXAMPLE 11 (COMPARATIVE)

Cyclic trimer ($D_3$, 2.5 g, 11.2 mmol), 1,1,3,3-tetramethyldisiloxane ($M^HM^H$, 2.8 g, 22.4 mmol) and $CF_3COOH$ (3 microliters) were mixed together and stirred at 50° C. Samples were removed at timed intervals for GC analysis. After 50 hours, the reaction mixture comprised 35.6% $M^HM^H$, 34.0% $D_3$, and 24.6% $M^HD_3M^H$.

EXAMPLE 12

Cyclic trimer ($D_3$, 2.5 g, 11.2 mmol), 1,1,3,3-tetramethyldisiloxane ($M^HM^H$, 2.8 g, 22.4 mmol) and LPNC (15 microliters of a 2% solution in 50 cstk dimethylsilicone oil) were mixed together and dissolved in THF (1.0 g), then stirred at 50° C. Samples were removed at timed intervals for GC analysis. After 48 hours, the reaction mixture comprised 14.0% $M^HM^H$, 11.4 % THF, 2.4% $D_3$, 65.8% $M^HD_3M^H$ and 2.4% $M^HD_6M^H$.

EXAMPLE 13

Cyclic trimer ($D_3$, 2.5 g, 11.2 mmol), 1,1,3,3-tetramethyldisiloxane ($M^HM^H$, 2.8 g, 22.4 mmol), and methanesulfonic acid (2 microliters) were mixed together and stirred at 50° C. Samples were removed at timed intervals for GC analysis. After 20 h the reaction mixture comprised 20.0% $M^HM^H$, 1.0% $D_3$, 73.5% $M^HD_3M^H$ and 1.2% $M^HD_6M^H$.

While preferred embodiments have been shown and described, various modifications and substitutions may be made thereto without departing from the spirit and scope of the invention. Accordingly, it is to be understood that the present invention has been described by way of illustration and not limitation.

I claim:

1. A method for the manufacture of low molecular weight dialkyl hydrogen siloxanes, comprising an acid-catalyzed ring opening of a cyclic alkylsiloxane in the presence of tetraalkyldisiloxane to form $(R_2HSiO)(SiR'_2O)_3(SiHR_2)$ wherein R and R' are each independently monovalent alkyl groups having from 1 to 12 carbon atoms or halogen-substituted alkyl groups having from 1 to 12 carbon atoms.

2. The method of claim 1, wherein R and R' are each independently monovalent alkyl groups having from one to three carbon atoms or halogen-substituted alkyl groups having from one to three carbon atoms.

3. The method of claim 1, wherein R and R' are methyl.

4. The method of claim 1, wherein the reaction is at about 50° C.

5. The method of claim 1, wherein the ratio of tetraalkyldisiloxane to cyclic alkylsiloxane is about 1:2.

6. The method of claim 1, wherein the acidic catalyst has a $pK_a$ in the range from about 0 to about −10.

7. The method of claim 1, wherein the acidic catalyst is selected from the group consisting of sulfonic acids and linear phosphonitrilic chloride.

8. The method of claim 1, wherein the acidic catalyst is methanesulfonic acid, toluenesulfonic acid, or linear phosphonitrilic chloride.

9. The method of claim 1, wherein the reaction is solventless.

10. A method for the manufacture of $(H(CH_3)_2SiO)(Si(CH_3)_2O)_3(Si(CH_3)_2)$ without rapid equilibration, comprising reacting 1,1,2,2-tetramethyldisiloxane and hexamethylcyclotrisiloxane in the presence of an acidic catalyst.

11. The method of claim 10, wherein the acidic catalyst is a sulfonic acid or linear phosphonitrilic chloride.

12. The method of claim 10, wherein the acidic catalyst is methanesulfonic acid, toluenesulfonic acid, or linear phosphonitrilic chloride.

13. The method of claim 10, wherein the ratio of 1,1,2,2-tetramethyldisiloxane to hexamethylcyclotrisiloxane is about 2:1.

14. The method of claim 10, wherein the reaction is solventless.

* * * * *